United States Patent [19]

Kuwabara et al.

[11] Patent Number: 5,364,409
[45] Date of Patent: Nov. 15, 1994

[54] ENDOSCOPIC NEEDLE HOLDER

[75] Inventors: Masayoshi Kuwabara, Ibaragi; Tomohiko Asahara, Tokyo; Noboru Ujiie; Nobuhiro Kagaminuma, both of Koriyama, all of Japan

[73] Assignee: Ethicon, Inc., Somerville, N.J.

[21] Appl. No.: 57,235

[22] Filed: May 4, 1993

[30] Foreign Application Priority Data

May 8, 1992 [JP] Japan .............. 4-037365[U]

[51] Int. Cl.⁵ .............................. A61B 17/04
[52] U.S. Cl. .................... 606/148; 606/144; 606/205
[58] Field of Search .......... 606/148, 144, 145, 146, 606/147, 205, 139; 112/169

[56] References Cited

U.S. PATENT DOCUMENTS

| | | | |
|---|---|---|---|
| 1,400,653 | 12/1921 | Barbour | 606/139 |
| 2,286,578 | 6/1942 | Sauter | 606/144 |
| 3,426,757 | 2/1969 | Shannon et al. | 606/139 |
| 3,985,138 | 10/1976 | Jarvik | 606/144 X |
| 4,596,249 | 6/1986 | Freda et al. | 606/145 |
| 5,147,373 | 9/1992 | Ferzli | 606/148 X |
| 5,261,917 | 11/1993 | Hasson et al. | 606/205 X |

FOREIGN PATENT DOCUMENTS 4127812  2/1993  Germany .............. 606/148

Primary Examiner—Michael H. Thaler
Attorney, Agent, or Firm—Paul A. Coletti

[57] ABSTRACT

The invention provides a needle holding arrangement for only the gripping of a needle within the body cavity. There is provided a suture fixing means for gripping or fixing a suture with a needle on an outer peripheral surface of the needle-holder shaft. After piercing and passing of the needle through the tissue in the body, a knot of the suture can be made within the body cavity, and saturation and ligation of tissues in the body and end closure and ligation of blood vessel and gall duct can also be performed.

3 Claims, 10 Drawing Sheets

ENDOSCOPIC NEEDLE HOLDER

FIELD OF THE INVENTION

The present invention relates to a needle holder for operation which is used mainly for operation under endoscopic surgery and laparoscopic surgery, and which is also effective in open surgery on parts of the body in which suturing is difficult, such as deep tissues. More specifically, the invention relates to a needle holder for operation which can be widely used not only for suturing tissue and ligation in the abdominal cavity, thoracic cavity and other body cavities but also suturing with or without a needle for closure of blood vessels, gall ducts, etc.

BACKGROUND OF THE INVENTION

In endoscopic operation in the abdominal cavity, inert gases such as carbon dioxide gases are introduced into the abdominal cavity and slightly pressurized to effect a so-called pneumoperitoneum. Or, the opening abdominal wall is mechanically raised to secure an opening within the abdominal cavity whereby an appliance for operation, monitoring or the like is inserted into the abdominal cavity. Therefore, first, a trocar with a circular hole and a valve is pierced through the abdominal wall from the outside of the body.

After the trocar has been pierced into the abdominal wall, an appliance such as a gripping forceps, a sawtooth shearing knife, a suturing forceps, a biopsy forceps, and a tearing forceps for various operations and diagnoses such as tissue sampling is introduced into the body cavity. In the case where a suture is used within the body cavity, a suture with a needle having a straight or a curved shape adjusted to the type of operation is used, along with a needle holder for operating the needle.

A conventional needle holder is designed so that a needle holding portion capable of being opened and closed to grip the needle is provided at the distal end of a needle-holder shaft, and the proximal end is provided with an operating handle, so that the needle holding portion is operated by the operating handle whereby a needle carrying a suture thereon is gripped by the needle holding portion.

SUMMARY OF THE INVENTION

The conventional needle-holder for operation has been configured as described above. In operation, the needle holding portion is inserted into the body cavity through a trocar. However, in the conventional needle holder, the needle is merely gripped by the needle holding portion, and therefore, the needle inserted from the trocar can be gripped by the needle holding portion and the needle can be pierced into the tissue. However, thereafter, it is rarely possible to make a knot of the thread within the body cavity to effect ligation of the tissue in the body.

In the case where ligation is intended, the end of the suture on the pierced side is removed from the body cavity through the trocar tube to make a knot, after which it is passed through the trocar and again fed into the body cavity. Or, two or more forceps make a knot within the body cavity using three or more needle holders. Yet, these operations are complicated or difficult under pneumoperitoneum. For this reason, endoscopic ligation and closure are generally accomplished by a metallic clip in place of a suture, even though it may be desirable to suture.

This invention has been accomplished in order to enable the above-described task. It is an object of this invention to provide a needle holder which can grip a suture on a needle within the body cavity, which can make a knot of the suture with a needle within the body cavity after the needle has been pierced into the tissue in the body and which enables suturing and ligation of tissue within the body during operation and end closure and ligation of blood vessels and the gall duct.

According to the present invention, there is provided a needle holder wherein a suture fixing means for gripping and fixing a suture is provided on an outer peripheral surface of the needle-holder shaft.

In the needle holder according to the present invention, a part of the suture end without the needle is secured to a suture fixing means on the needle holder shaft. The needle is operated by a needle holding portion inserted into the body cavity together with the suture on a needle (through a trocar). Thereafter, the suture on the piercing side of the tissue (the side into which the needle first pierces of the tissue in the body) is gripped, after which the needle is drawn and pulled around the suture by a separate needle holder or the like, thus making a knot as desired. This operation may be repeated two or three times. Even in the case where a special knot is made, a part of the end with the needle can be gripped and fixed.

Further, the suture on the secondary piercing side (the side in which a needle has pierced tissue) is brought into engagement with the suture fixing means on the needle holder shaft, the end of the suture is wound on the end of the needle holder shaft while gripping the suture by a separate needle holder or the like, after which the needle is pulled out of the central portion of the shaft on which the suture is wound, so that a knot can be likewise obtained.

DETAILED DESCRIPTION OF THE INVENTION

An embodiment of the present invention will be described hereinbelow with reference to the drawings.

Figure 1:
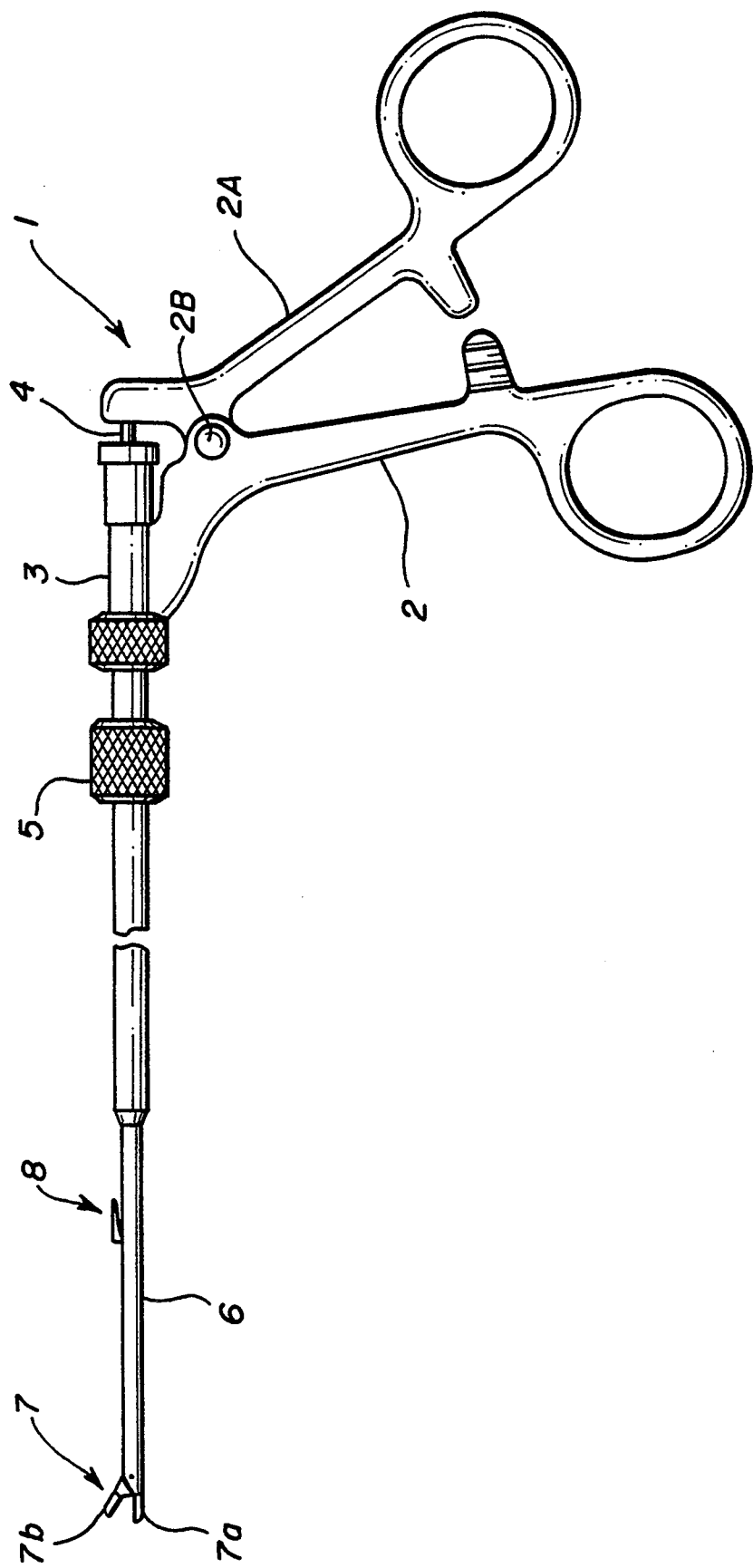
FIG. 1 is an external view of the whole structure of a needle holder according to a first embodiment of this invention.
Figure 2:
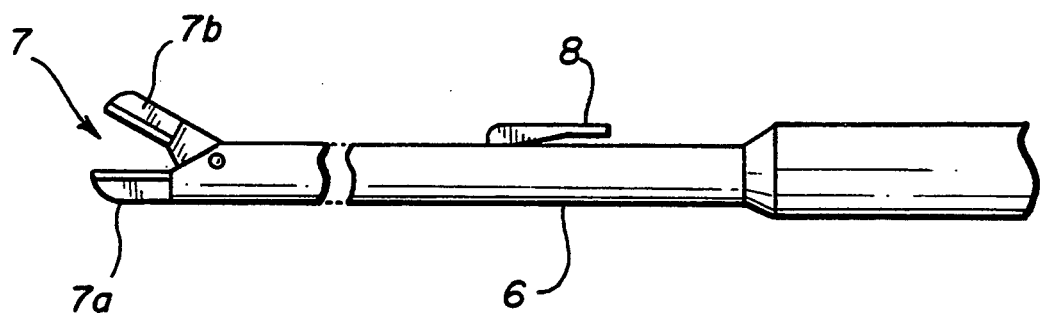
FIG. 2 is an external view showing a portion of the suture fixing means in an enlarged scale.

FIG. 1 is an external view of the whole structure showing a needle holder 1 for operation according to a first embodiment of the present invention, and FIG. 2 is an external view showing a portion of the suture fixing means of FIG. 1 in an enlarged scale.

In the drawings, reference numeral 1 designates a body of a needle holder. The needle holder 1 comprises operating handles 2, 2A and a core or shaft 4 on the proximal end for transmission of an operating force caused motion of handle 2A around hollow shaft portion 3 at pivot 2B on handle 2.

In the needle holder 1, a sleeve-like needle holder shaft 6 is detachably connected to the extreme end of the shaft portion 3 on the distal end through a coupling member 5 such as a cap nut.

A needle holding portion 7 for gripping a needle with a suture attached is provided on the extreme distal end of the needle holder shaft 6.

This needle holding portion 7 comprises a fixed needle holding element portion 7a and a movable needle holding element portion 7b, and an internal core (not shown) slidable through shafts 3, 6 for transmission of power to the movable needle holding element portion 7b from core 4 on the proximal side of the instrument through a coupling member (not shown) connected to handle 2A.

In the needle holder 1 configured as described above, a suture fixing means 8 is provided on an outer peripheral surface of the needle holder shaft 6.

The suture fixing means 8 is formed integral with the needle holder shaft 6 and comprises a catch element bent away from the needle holding portion 7 so that a part of the suture is temporarily gripped and fixed within the body cavity adjacent to the outer peripheral surface of the needle holder shaft 6.

The suture fixing means 8 is positioned in the range of 30 mm to 200 mm, more preferably, 30 to 100 mm from the distal end of needle holder 1.

Figure 3:
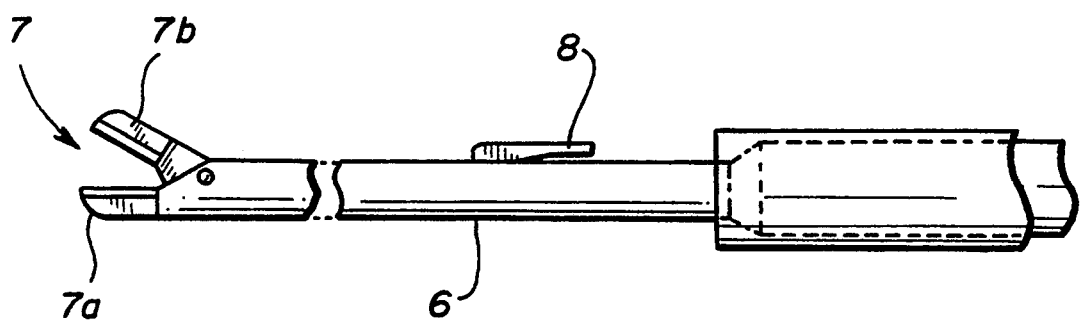
FIG. 3 is a side view of the needle holder.
Figure 4:
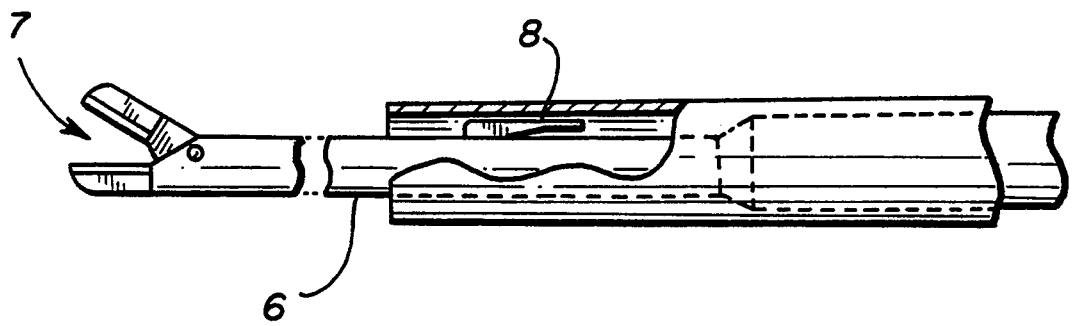
FIG. 4 is a side view showing a trocar inserted about the needle holder.
Figure 5:
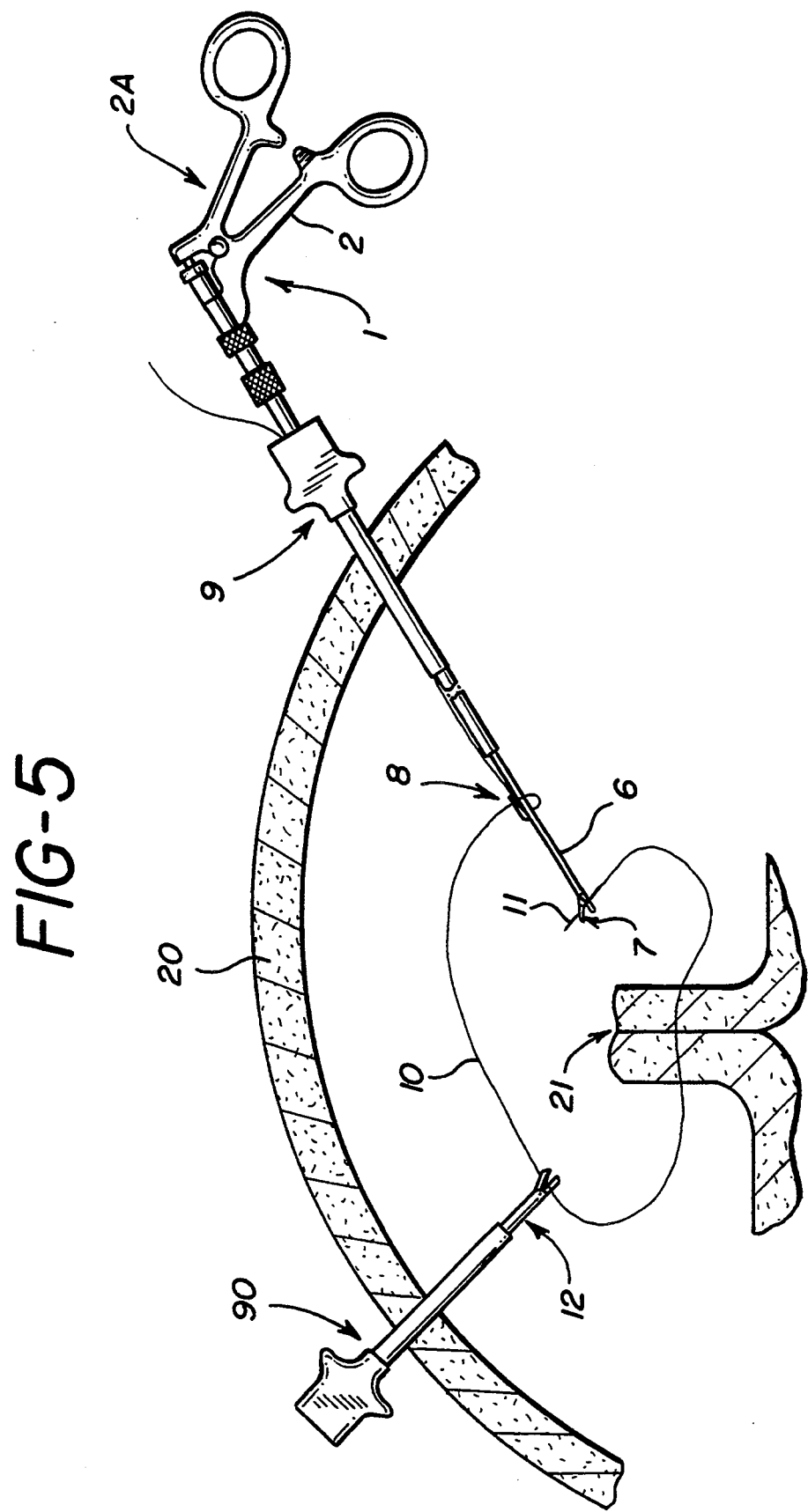
FIG. 5 is an view of the needle holder in use according to this invention.

In FIGS. 3 and 4, reference numeral 13 denotes an outer tube slidably slipped over the needle holder shaft 6. This outer tube 13 covers the suture fixing means 8 at an advanced position. In FIG. 5, reference numeral 9 denotes a trocar to be pierced and passed through the cavity wall such as the abdominal cavity and the thoracic cavity. The needle holder shaft 6 is inserted into the trocar 9.

The operation will be described below. As a first method used, for example, in an operation within the body cavity such as an endoscopic operation, generally, as shown in FIG. 5, the required number (two in the illustration) of trocars 9 and 90 are pierced and passed through a body cavity wall 20.

In the present needle holder, a needle 11 holding a suture 10 is gripped by the needle holding portion 7 at the extreme end of the needle holder shaft 6, and a part of a free end of the suture 10 is placed in and fixed by the suture fixing means 8 on the needle holder shaft 6.

After the a part of the suture 10 has been fixed onto the needle holder shaft 6, the needle holder shaft 6 is inserted into the body cavity together with the suture 10 on needle 11 through the trocar 9 which has already pierced through the body cavity wall as mentioned above. In this case, a separate needle holder 12 is inserted from the other trocar 90. This needle holder 12 may be a conventional structure or the same structure as that of the present invention.

Figure 6:
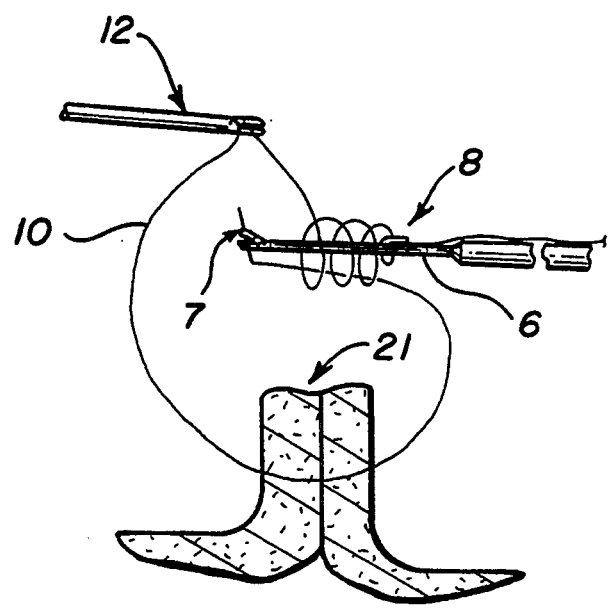
FIG. 6 is an view showing the suture being wound.

Then, the needle holding portion 7 at the extreme end of the needle holder shaft 6 is operated within the body cavity by the operating handles 2, 2A whereby the needle 11 is pierced and passed through the tissue 21 in the body. Thereafter, the suture 10 which has exited the tissue 21 is wound around the needle holder shaft 6 by the separate needle holder 12 while gripping the needle 11 (see also FIG. 6).

Figure 7:
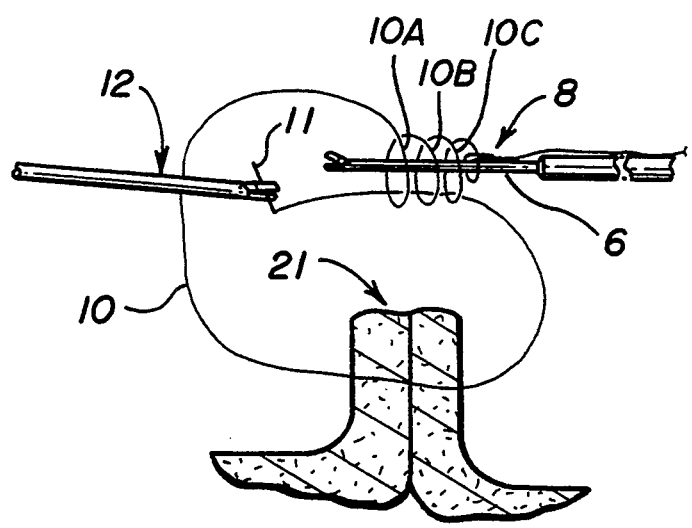
FIG. 7 is an view showing the ligation of tissue.

Thereafter, as shown in FIG. 7, the needle 11 is transferred to needle holder 12, and pulled in the direction of needle holder 12, to create a knot at the end loops of the suture 10A, 10B, 10C. This operation, of course, may be repeated two, three, or more times.

Figure 8:
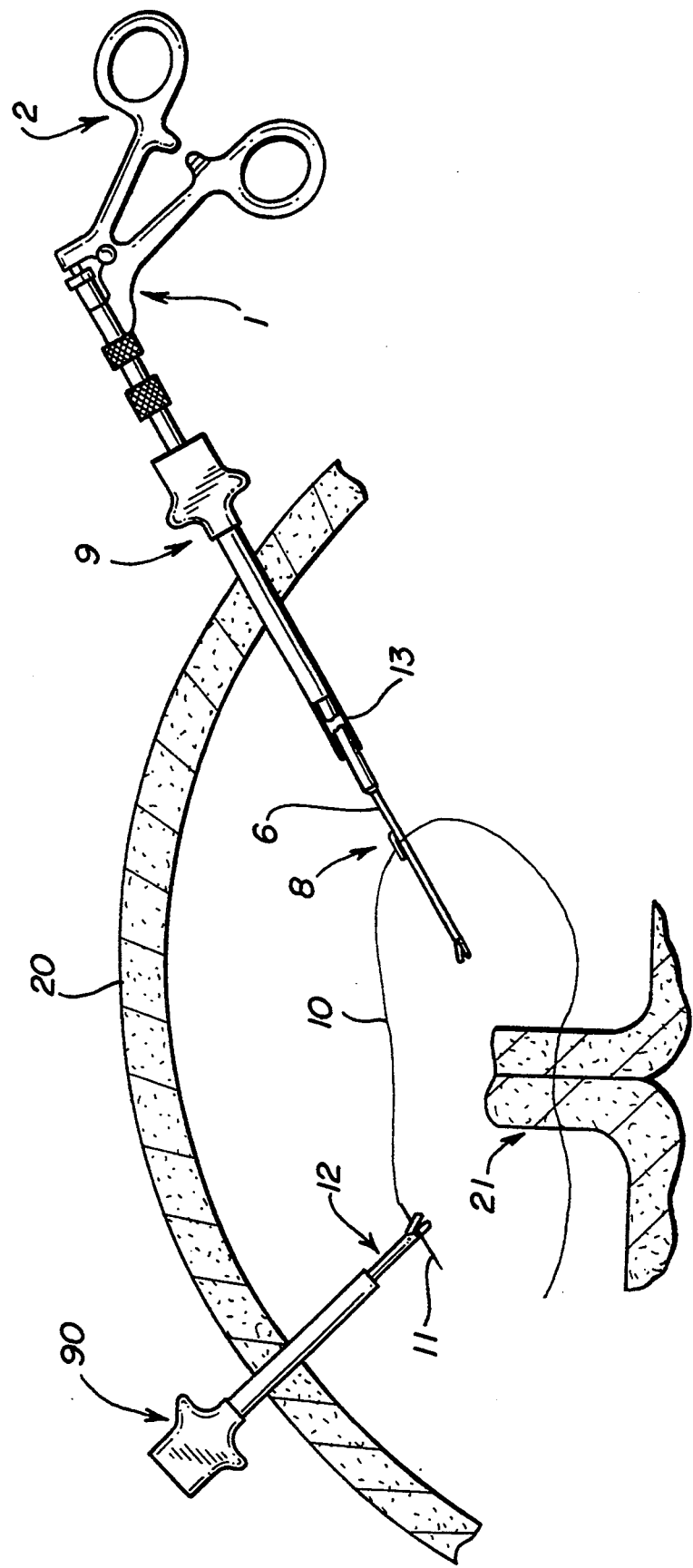
FIG. 8 is an view showing a second method of use of the needle holder according to the present invention.
Figure 9:
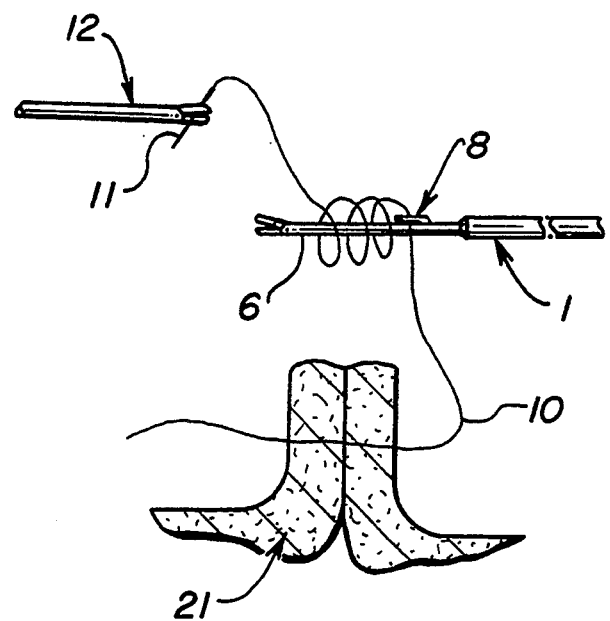
FIG. 9 is an enlarged view showing the suture being wound.
Figure 10:
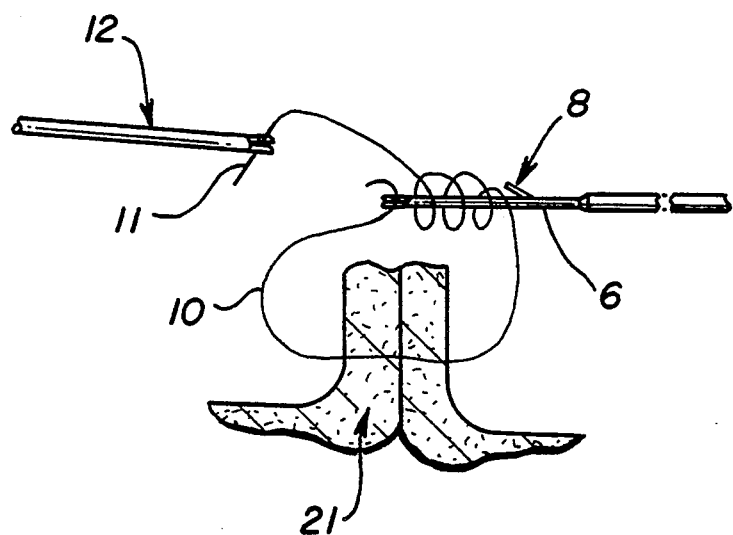
FIG. 10 is an explanatory view showing the tissue being ligated.

A second method will be described below with reference to FIGS. 8 to 10.

According to the second method, a suture 10 from one side of the tissue 21 in the body is brought into engagement with suture fixing means 8 on a needle holder shaft 6. The suture 10 is wound about the distal end of the needle holder shaft 6, as shown in FIG. 9, while gripping the needle 11 at the distal end of the suture 10 by a separate needle holder 12. Thereafter, as shown in FIG. 10, the suture 10 is pulled from the wound area by needle holder 12. Thus, a desired knot is likewise obtained.

Figure 11:
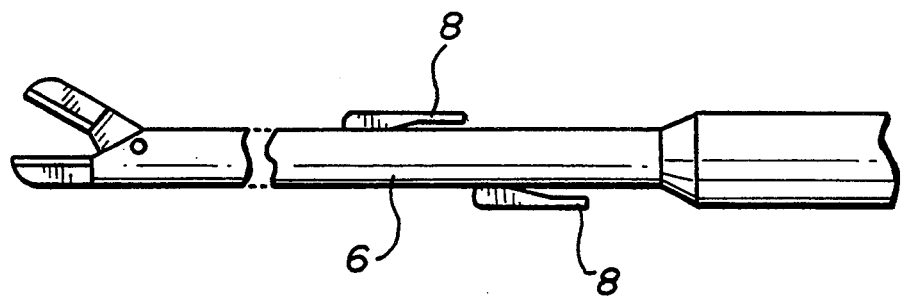
FIG. 11 is a plan view of the needle holder according to a second embodiment of this invention.

FIG. 11 shows a second embodiment according to the present invention. In the second embodiment, two suture fixing means 8 are provided at different positions in the axial direction of the shaft 6 of the needle holder.

Figure 12:
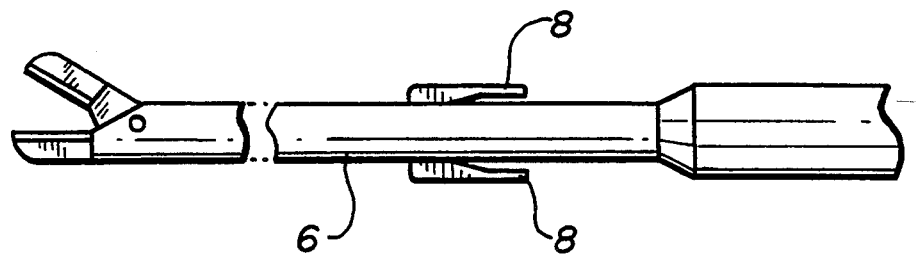
FIG. 12 is a plan view of a needle holder according to a third embodiment of this invention.

FIG. 12 shows a third embodiment according to the present invention. In the third embodiment, two suture fixing means 8 are provided at axial symmetrical positions on the needle holder shaft 6.

Figure 13:
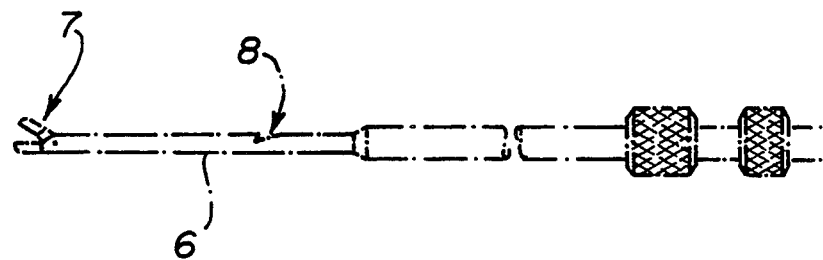
FIG. 13 is a plan view of a needle holder according to a fourth embodiment of this invention.
Figure 14:
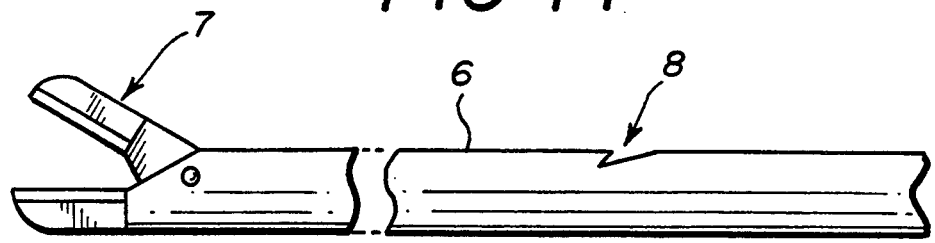
FIG. 14 is an enlarged view of the end of the needle holder of FIG. 13.

FIGS. 13 and 14 show a fourth embodiment. The suture fixing means 8 according to the fourth embodiment comprises a cut groove formed in the outer peripheral surface of the needle holder shaft 6.

Figure 15:
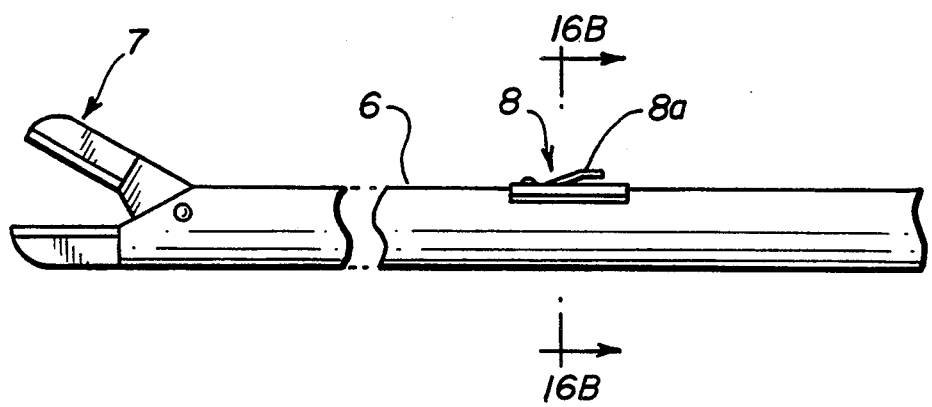
FIG. 15 is a plan view of a needle holder according to a fifth embodiment of this invention.
Figure 16A:
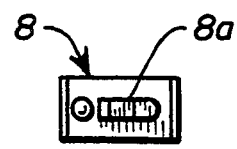
FIG. 16(A) is an elevation view of a suture fixing means as in FIG. 15.
Figure 16B:
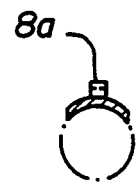
FIG. 16(B) is an cross-sectional view according to lines 16B—16B of FIG. 15.

FIGS. 15, 16A and 16B show a fifth embodiment of this invention. The suture fixing means 8 according to the fifth embodiment comprises a clip on which is integrally formed a raised element portion 8a for fixing a suture separately from the needle holder shaft 6. This clip is mounted on the needle holder 6 by a screw or the like.

Figure 17:
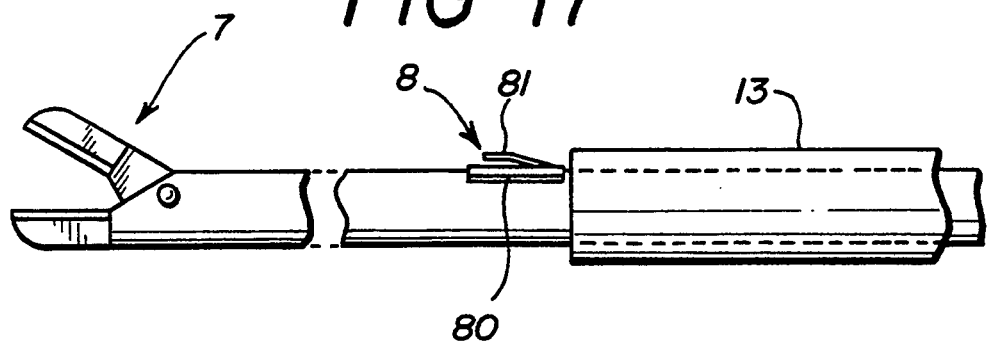
FIG. 17 is a plan view of a needle holder according to a sixth embodiment of this invention.
Figure 18:
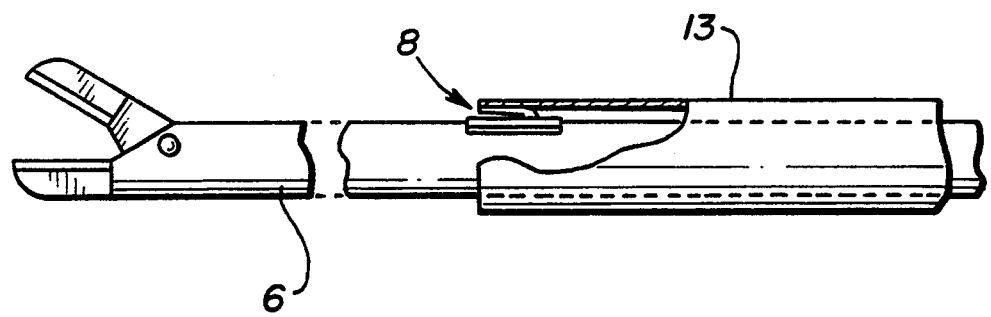
FIG. 18 is a plan view of the function of the embodiment of FIG. 17.

FIGS. 17 and 18 shows a sixth embodiment of this invention. The suture fixing means 8 according to the sixth embodiment comprises a base 80 mounted and fixed to the needle holder shaft 6, and a clip element 81 formed integral with the base 80 and bent toward the needle holding portion 7. This clip 81 has an elastic spring force to a raised position shown in FIG. 17.

In case of the suture fixing means 8 as described above, in FIG. 17, after the suture 10 has been engaged with the clip element 81, the outer tube 13 is slidably moved forward, and the clip element 81 is held down by the outer tube 13 whereby the suture 10 is retained by the clip element 81.

As described in connection with FIGS. 8 to 10, when the outer tube 13 is slidably moved backward after a knot of the suture 10 has been made, pressing of the clip element 81 caused by the outer tube 13 is released so that the suture 10 is smoothly released.

Figure 19:
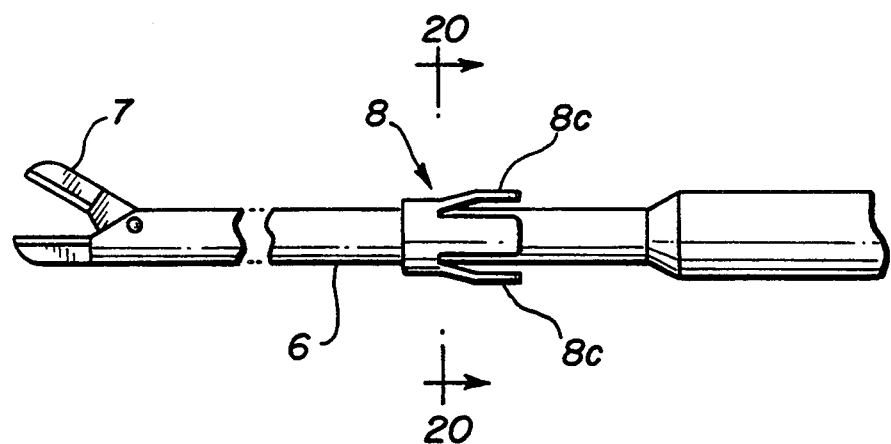
FIG. 19 is a plan view of a needle holder according to a seventh embodiment according to this invention.
Figure 20:
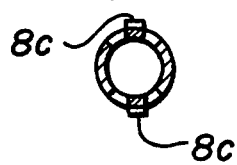
FIG. 20 is a cross-sectional view according to lines 20—20 of FIG. 19.

FIGS. 19 and 20 shows a seventh embodiment of this invention. The suture fixing means 8 according to the seventh embodiment comprises a ring having a plurality of catch elements 8c. This ring is detachably fitted and mounted on the needle holder shaft 6.

Figure 21:
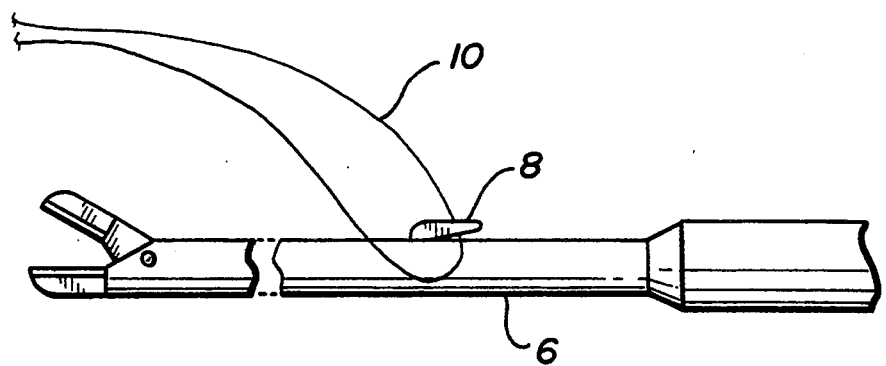
FIG. 21 is a plan view of a needle holder according to an eighth embodiment according to this invention.
Figure 22:
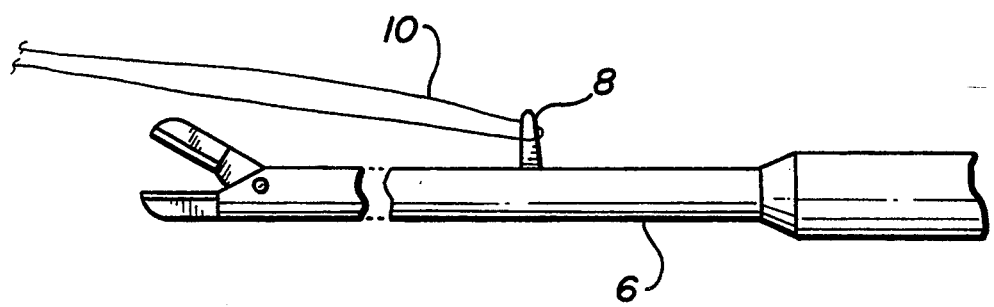
FIG. 22 is a plan view of the holder of FIG. 21 when a suture is released.
Figure 23:
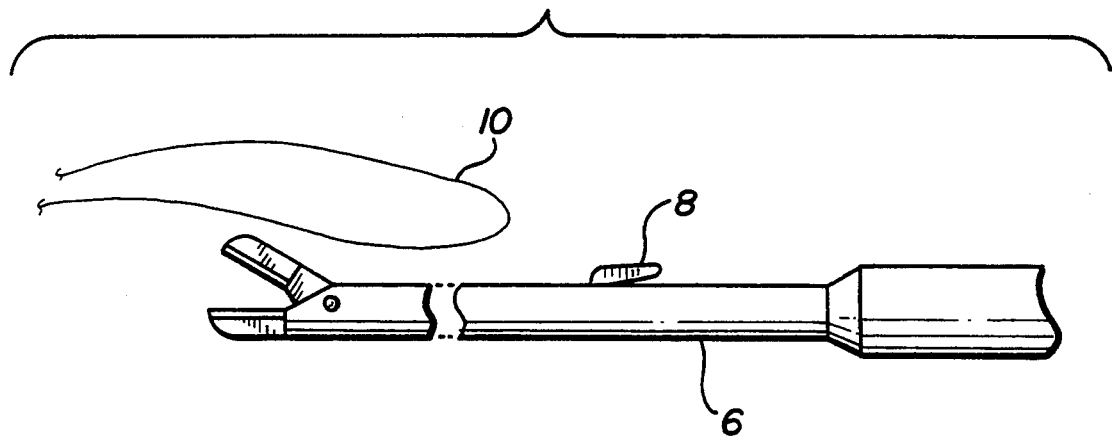
FIG. 23 is a plan view of the holder of FIG. 21 showing the device when a suture has been released.

FIGS. 21 to 23 show an eight embodiment of this invention. The suture fixing means 8 according to the eighth embodiment comprises a catch element which is provided rotatably back and forth on the needle holder shaft 6. The catch element 8 is urged by a spring (not shown) toward the position as shown in FIG. 21.

Accordingly, the suture 10 is caught by the catch element 8 as in the state shown in FIG. 21 to make a knot, after which the suture 10 is pulled by the needle holder. Then, the catch element 8 is rotated as shown in FIG. 22 whereby the suture 10 is smoothly released from the catch element 8. And, after the release, the catch element 8 is rotated and returned to the state shown in FIG. 21.

In any of the suture fixing means 8 described in the forementioned embodiments, a suture with a needle is held to thereby fix the suture, which corresponds to a different coarseness of threads. Since coarseness No. 0 to No. 5 are generally used, a gap required is from 0.10 mm to 0.4 mm, which fulfills the dimensional requirement of fitting through a trocar cannula.

The fixing or knotting force on a suture by the suture fixing means 8 is a tension applied when a knot is made. Normally, the force is strong enough to withstand tension equivalent to pulling a mass in the range of 0.05 to 1.2 kg. Any constructions of the needle holder corresponding thereto will suffice, and accordingly, the first to eighth embodiments are merely illustrated as preferred embodiments.

In the case where the needle holder according to the present invention is actually used, generally, as described above, the needle 11 at the end of the suture 10 is gripped by the needle holding portion 7 and a part of the suture 10 is fixed to the fixing means 10, after which it is passed through the trocar 9. However, alternatively, the suture 10 is not fixed; only the needle 11 is gripped by the needle holding portion 7 and passed through the trocar 9, after which it is gripped at a suitable length from the end of the needle.

From the foregoing, the suture fixing means 8 in the above-described embodiments displays important functions such as gripping a part of the suture 10 and application of tension when a knot is drawn.

Without the suture fixing means 8, the suture with a needle cannot be gripped in a preferable force and direction within the body cavity, and a reliable ligation with a knot firmly tied cannot be carried out.

While the needle holder according to the present invention is used mainly for endoscopic surgery, it is to be noted needless to say that the needle holder also is effective for "open" body parts where suturing is difficult to perform, such as deep tissues, or even in laparotomy and thoracotomy.

Further, the needle holder 1 according to the present invention is widely used both for sutures with or without a needle not only in suturing tissue and ligation in endoscopic operation, but for closure and ligation of blood vessels and the gall duct.

Thus, as described above, according to the present invention, suture fixing means for at least temporarily gripping and fixing a suture is provided on the outer peripheral surface of a needle holder shaft having a needle holding portion capable of gripping a suture on a needle at its extreme end. A part of the suture is secured to the fixing means, and the needle is operated by a needle holding portion inserted into the abdominal cavity together with the suture (through a trocar). The suture is wound around the needle holder shaft while gripping the needle after being passed through tissue. Thereafter, the needle is pulled out in the direction of the distal end by a separate needle holder, to make a knot as desired.

Furthermore, a suture is caught by fixing means on the needle holder shaft, and the end of the suture is wound on the distal end of the needle holder of the present needle holder, while gripping the end of the suture by a separate needle holder or the like. Then, the suture is pulled out of the wound while holding the extreme end of the suture by the present needle holder, whereby a desired knot can likewise be made.

We claim:

1. An endoscopic needle holder comprising:
   an elongated shaft having proximal and distal ends;
   a pair of needle holding jaws extending from the distal end of said shaft;
   an actuation mechanism for operating the needle holding jaws, extending from said shaft proximal end; and
   a suture holding mechanism extending from said shaft, said suture holding mechanism comprising a pair of hooks spaced diametrically apart on said shaft and extending toward said shaft proximal end.

2. The holder of claim 1 wherein said suture holding mechanism is positioned near said shaft distal end.

3. The holder of claim 1 wherein said hooks are located at different of distal positions along said shaft.

* * * * *